(12) United States Patent
Alix et al.

(10) Patent No.: US 11,584,926 B2
(45) Date of Patent: Feb. 21, 2023

(54) METHOD AND SYSTEM FOR MAGNETIC EXTRACTION OF COMPONENTS IN A LIQUID SAMPLE

(71) Applicant: BIOMÉRIEUX, Marcy l'Etoile (FR)

(72) Inventors: David Alix, Gosné (FR); Edgar Minassian, Lentilly (FR); Jean-Claude Raymond, Bessenay (FR); Philippe Wandels, Lyons (FR)

(73) Assignee: BIOMÉRIEUX, Marcy l'Etoile (FR)

( * ) Notice: Subject to any disclaimer, the term of this patent is extended or adjusted under 35 U.S.C. 154(b) by 306 days.

(21) Appl. No.: 17/110,436

(22) Filed: Dec. 3, 2020

(65) Prior Publication Data

US 2021/0115433 A1 Apr. 22, 2021

Related U.S. Application Data

(62) Division of application No. 16/098,095, filed as application No. PCT/EP2016/078905 on Nov. 25, 2016.

(30) Foreign Application Priority Data

May 3, 2016 (EP) .................................... 16168001
Jul. 22, 2016 (EP) .................................... 16180724

(51) Int. Cl.
*C12N 15/10* (2006.01)
*B01L 3/02* (2006.01)
(Continued)

(52) U.S. Cl.
CPC ........ *C12N 15/1013* (2013.01); *B01L 3/0231* (2013.01); *B01L 3/0275* (2013.01);
(Continued)

(58) Field of Classification Search
CPC ....... B01L 2300/041; B01L 2300/0609; B01L 2300/0848; B01L 3/0231; B01L 3/0275;
(Continued)

(56) References Cited

U.S. PATENT DOCUMENTS 5,234,809 A 8/1993 Boom et al.
8,187,460 B2 5/2012 Kreuwel et al.
(Continued)

FOREIGN PATENT DOCUMENTS

EP 1 081 234 A2 3/2001
EP 1 455 191 A1 9/2004
(Continued)

OTHER PUBLICATIONS

Jan. 22, 2021 Office Action issued in U.S. Appl. No. 16/098,095.
(Continued)

*Primary Examiner* — Jennifer Wecker
*Assistant Examiner* — Jonathan Bortoli
(74) *Attorney, Agent, or Firm* — Oliff PLC

(57) ABSTRACT

A pipette holder that includes: (i) a base; (ii) a recess made in the base, which can removably house a well support; (iii) a pipette support comprising a first housing into which can be inserted a pipette equipped with one or more tubular pipette cones that each comprise a tip intended for pipetting liquid, the first housing opening out onto the recess of the base, the pipette support being translationally mobile relative to the base in a direction parallel to an axis of the pipette cones and mobile between a first position in which the tip of each pipette cone is inserted in a well of the well support and at least one second position in which the tip is outside the well; and (iv) a second housing which can removably house a magnetized part.

17 Claims, 11 Drawing Sheets

(51) Int. Cl.
*B01L 3/00* (2006.01)
*B01L 9/00* (2006.01)
*C12Q 1/6806* (2018.01)
*G01N 1/40* (2006.01)

(52) U.S. Cl.
CPC ........... *B01L 3/50853* (2013.01); *B01L 9/523* (2013.01); *B01L 9/543* (2013.01); *C12Q 1/6806* (2013.01); *B01L 2300/041* (2013.01); *B01L 2300/0609* (2013.01); *B01L 2300/0848* (2013.01); *G01N 1/4077* (2013.01)

(58) Field of Classification Search
CPC ...... B01L 3/50853; B01L 9/523; B01L 9/543; C12N 15/1013; C12Q 1/6806; C12Q 1/6883; C12Q 2600/156; C12Q 2600/158; G01N 1/4077
See application file for complete search history.

(56) References Cited

U.S. PATENT DOCUMENTS

| | | | |
|---|---|---|---|
| 2003/0012699 | A1 | 1/2003 | Moore et al. |
| 2008/0095671 | A1 | 4/2008 | Mathus et al. |
| 2009/0071266 | A1 | 3/2009 | Nelson et al. |
| 2009/0074622 | A1 | 3/2009 | Kalamakis et al. |
| 2010/0006509 | A1* | 1/2010 | Hornes ................. B03C 1/0335 210/695 |
| 2011/0076205 | A1 | 3/2011 | Kelly et al. |
| 2013/0043191 | A1* | 2/2013 | Park ................... C12N 15/1003 210/695 |
| 2015/0266658 | A1* | 9/2015 | Tajima ............... G01N 35/1065 222/1 |

FOREIGN PATENT DOCUMENTS

| | | |
|---|---|---|
| EP | 1 992 689 A1 | 11/2008 |
| EP | 1 589 105 B1 | 11/2009 |
| JP | 2008-220260 A | 9/2008 |
| JP | 2012-152213 A | 8/2012 |
| WO | 03/006168 A1 | 1/2003 |
| WO | 2007/051859 A1 | 5/2007 |
| WO | 2014/072438 A1 | 5/2014 |
| WO | 2014/083165 A1 | 6/2014 |

OTHER PUBLICATIONS

Apr. 6, 2022 Office Action issued in U.S. Appl. No. 16/098,095.
Jul. 16, 2021 Office Action issued in U.S. Appl. No. 16/098,095.
Boom et al., "Rapid and Simple Method for Purification of Nucleic Acids," Journal of Clinical Microbiology, Mar. 1990, vol. 28, No. 3, pp. 495-503.
Jan. 26, 2017 International Search Report issued in International Patent Application No. PCT/EP2016/078905.
Jan. 26, 2017 Written Opinion of the International Searching Authority issued in International Patent Application No. PCT/EP2016/078905.

* cited by examiner

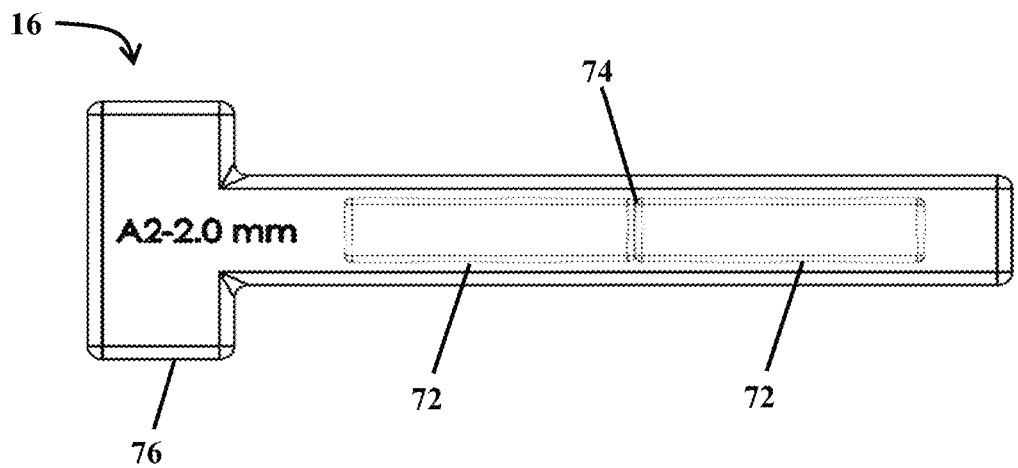
Figure 7
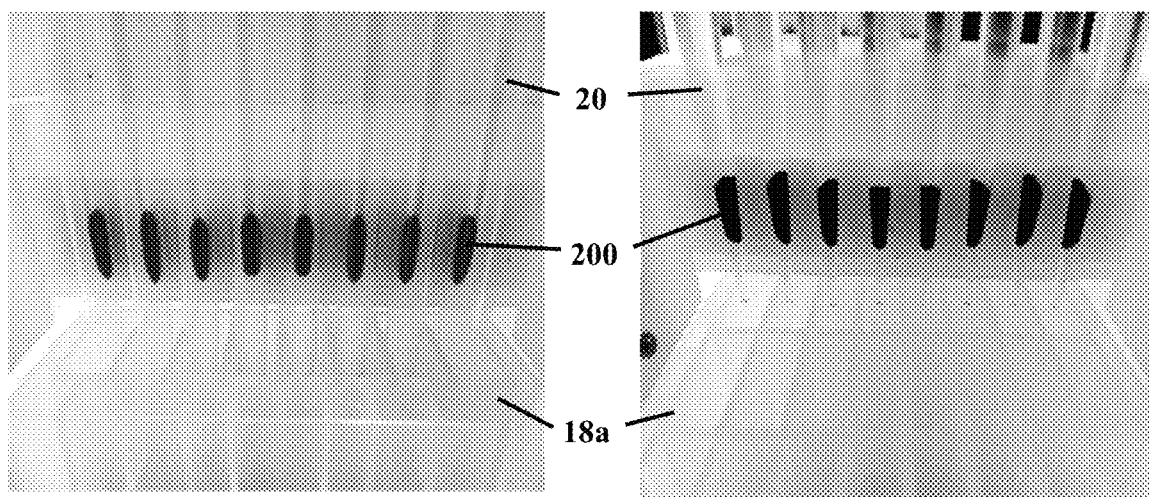
Figure 9
Figure 10
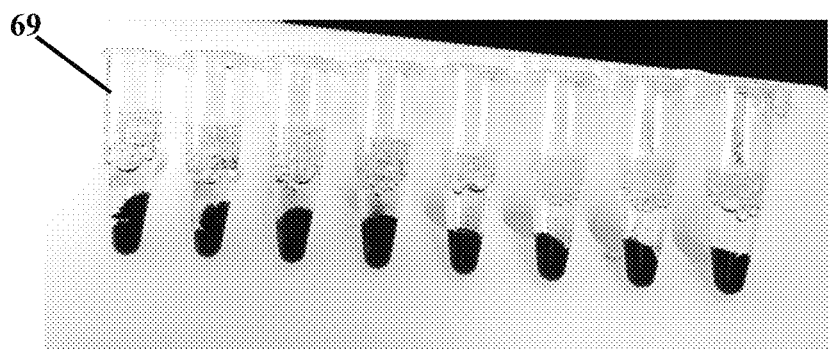
Figure 11

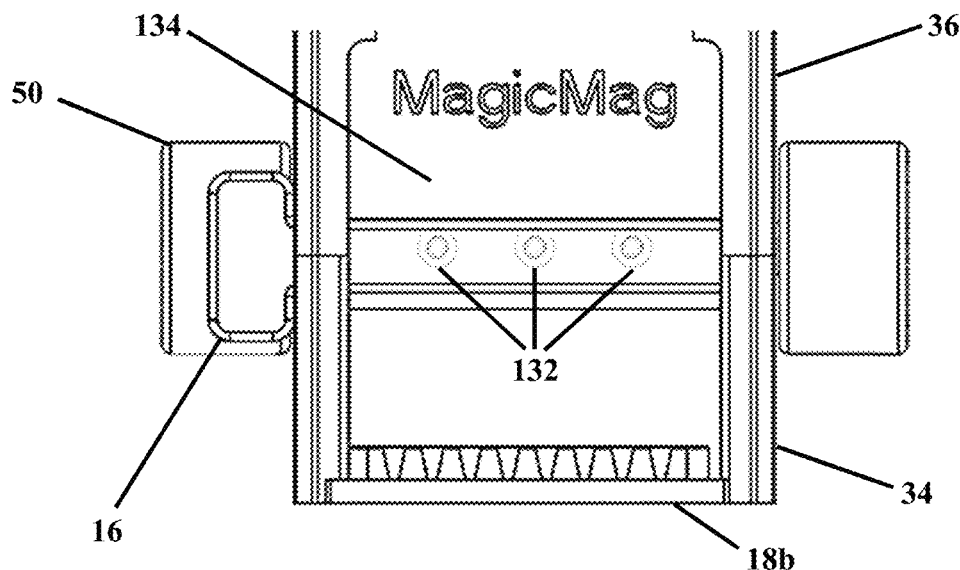
Figure 12C
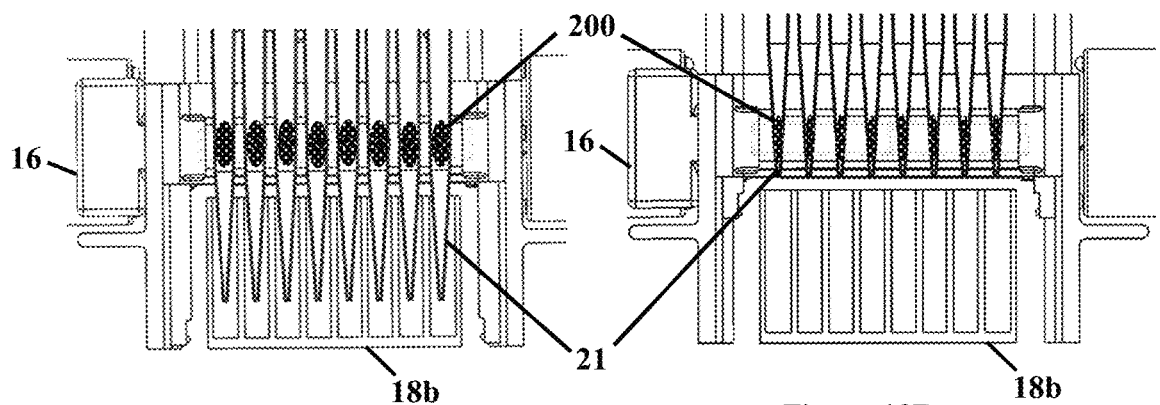
Figure 13A
Figure 13B
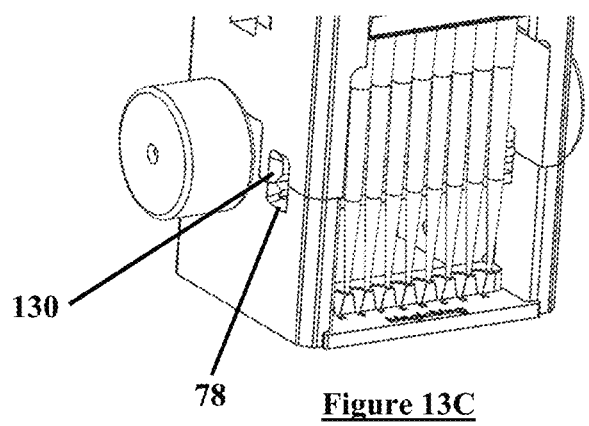
Figure 13C

METHOD AND SYSTEM FOR MAGNETIC EXTRACTION OF COMPONENTS IN A LIQUID SAMPLE

This is a Divisional of application Ser. No. 16/098,095 filed Oct. 31, 2018, which is a National Stage Entry of PCT/EP2016/078905 filed Nov. 25, 2016, and claims priority to EP 16180724.3 filed Jul. 22, 2016 and EP 16168001.2 filed May 3, 2016. The entire disclosures of the prior applications are hereby incorporated by reference in their entireties.

FIELD OF THE INVENTION

The invention relates to the field of the extraction of components contained in a solution using magnetic particles.

The invention can in particular be used in the biological sample preparation field, in particular in the implementing of in vitro diagnosis, by capturing analytes of biological origin (nucleic acids, microorganisms, proteins, peptides, etc) present in a solution.

PRIOR ART

Originally developed for the extraction of nucleic acids present in a biological sample and described in document U.S. Pat. No. 5,234,809, the "BOOM®" technology consists in introducing, into a liquid sample, magnetic particles capable of binding with components of interest, then in separating the magnetic particles from the sample by means of one or more magnets. The particles thus captured can then undergo a subsequent treatment, for example to release their components into a recovery solution. Because of the efficiency of this technique, many devices have been developed and marketed, in particular for DNA and RNA, etc.), these being both manual devices (for example the NucliSENS-miniMAG® from the applicant) and automated devices (NucliSENS-easyMAG® from the applicant). However, these automated devices have various limitations.

A first limitation concerns their polyvalence and their bulkiness. Indeed, these devices are usually heavy and bulky automated devices which are designed for carrying out a sequence of treatments that cannot be modified by the user. An automated device is thus designed for a single type of extraction, for example designed for the purification of nucleic acids, but incapable of carrying out a magnetic immunoconcentration.

A second limitation concerns the circuits for injecting and suctioning the various liquids used during the extraction. Since the number of liquids is high, this implies circuits which are also numerous and/or complex. Furthermore, because of possible contaminations, these injection/suction circuits must be regularly cleaned, which implies taking the devices out of service.

A third limitation concerns the stirring operations which are carried out in order to obtain homogeneity of the sample comprising the magnetic particles before capture thereof, in order to maximize the capture by said particles of the analytes of interest or in order to efficiently wash the magnetic particles. This type of stirring usually requires complex mechanisms, for example based on mobile magnets which cause the magnetic particles to move.

The fourth limitation concerns the various liquids used during the extraction. Usually, the steps carried out for the extraction are performed in or starting from a single container. As a result, this container fixes an identical volume for all the liquids involved (e.g. the sample, the various washing solutions, the eluting solution, etc), which limits the overall efficiency of the extraction process. Indeed, some treatments (e.g. washing) require large volumes in order to be completely efficient, whereas other treatments only need a small volume of liquid (e.g. the elution).

SUMMARY OF THE INVENTION

The objective of the present invention is to provide a method for extraction of components in a liquid sample by means of magnetic particles which offers great freedom in the choice of the liquid volumes, in particular up to 10 ml, used during the extraction.

To this effect, a subject of the invention is a method for extracting components contained in a biological sample in liquid form, said components being capable of binding to magnetic particles, the method comprising:
- a phase of mixing the sample with the magnetic particles;
- a phase of suctioning the mixture from a well in a tubular pipette cone comprising a tip intended for pipetting liquid;
- a phase of capturing the magnetic particles on an internal wall of the pipette cone:
   - by applying a first magnetic field to the pipette cone, said field being capable of attracting and holding the magnetic particles in a predetermined zone of the pipette cone, termed "capture" zone, above the tip of said cone;
   - and by applying at least one cycle of suction and discharge of the mixture contained in the pipette cone in a well;
- at least one phase of washing the particles captured on the internal wall of the pipette cone by:
   - discharging the mixture contained in the pipette cone; and
   - applying, from a well containing a washing solution, at least one cycle of suction and discharge of the washing solution in the pipette cone;
- a phase of migration of the magnetic particles on the internal wall of the cone, from the capture zone to the tip of the pipette cone, by carrying out a relative movement of the pipette cone relative to the first magnetic field;
- and a phase of transferring said magnetic particles having migrated into the tip of the pipette cone into a recovery well containing a solution.

In other words, the invention takes advantage of a pipette cone in which suction and discharge cycles can be carried out while dipping the tip of said pipette cone into a well. By virtue of such cycles, it is possible to capture all of the particles present in a sample of much greater volume than that of the volume, i.e. the cone, in which the extraction is carried out. It is even possible to pass through the cone a cumulative volume of liquid much greater than the volume of the sample itself, by regulating the number of suction and discharge cycles. Likewise, the volume of the washing solution(s) used, where appropriate, during the extraction can be much greater than the volume of the cone. The migration phase makes it possible, for its part, to localize the magnetic particles in a portion of the cone, the tip, which can dip into a well of very small volume. The volume of the recovery solution can therefore be small if necessary. The volume of the recovery solution is thus independent of the volume of the sample and of the volume of the pipette cone in which the extraction is carried out. By virtue of the invention, it is consequently possible to optimize each volume of liquid used, and thus to optimize the extraction.

Furthermore, because of the geometry of the tube-shaped cones and of the suction/discharge cycles, efficient stirring of the sample in the cones, said stirring being for example carried out before the capture, and also efficient washing, are obtained, this being without recourse to mechanisms of mobile magnet type. In addition, the inventors have noted that efficient washing is obtained in the cone even though the particles are captured on the wall of the pipette cone. A large volume of washing solution can be used, further increasing the efficiency of the washing. As a result, all the steps of the extraction (stirring, capture, washing, transfer into a recovery solution) can be carried out in the pipette cone.

According to one embodiment, the movement of the first magnetic field consists in moving the pipette cone parallel to a longitudinal axis of said cone, and in keeping the first magnetic field constant, the longitudinal axis of the pipette cone remaining at an equal distance from the first magnetic field during the movement of the pipette cone.

In other words, the migration of the particles can be carried out simply by moving the pipette cone relative, for example, to a permanent magnet.

According to one embodiment, the transferring phase comprises:
  placing the tip of the pipette cone in the recovery well;
  and applying a second magnetic field from the bottom of the recovery well so as to cause the magnetic particles contained in the tip of the pipette cone to migrate into the recovery well.

In particular, the second magnetic field is produced by a magnet positioned partially or entirely under the tip of the pipette cone. The first magnetic field applied to the pipette cone is deactivated during the application of the second magnetic field.

In other words, the second magnetic field makes it possible to simply attract the particles into the recovery well, which increases the speed of recovery of the magnetic particles in the recovery well, and also the number of particles recovered. Furthermore, the second magnetic field automatically captures the magnetic particles in the recovery well. For example, if the recovery solution is an eluent, the components bound to the particles have been released and a technician can directly pipette the solution which is free of magnetic particles.

According to one preferred variant, the transferring phase comprises the deactivation of the first magnetic field followed by the application of cycles of suction and discharge of the solution of the recovery well in the tip of the pipette cone, said application comprising:
  a first phase of applying the cycles at a first frequency;
  followed by a second phase of applying the cycles at a second frequency, lower than the first frequency.

The first phase makes it possible to efficiently disaggregate the clumps of particles captured on the pipette cone, also called "pellet", and thus to resuspend the particles in the recovery solution. The second phase makes it possible to continue to stir the solution while at the same time not opposing the migration of the particles under the effect of the magnetic field. This makes it possible to increase even further the speed of recovery and the number of particles recovered in the recovery well. Furthermore, if the solution is an eluent, the function of which is to release the components captured by the magnetic particles, these cycles have the effect of stirring the particles in the eluent, which increases the efficiency of the eluent, in particular when an eluting solution is used in the detaching of the analytes from the magnetic particles without a heating step.

According to one embodiment, the method comprises, prior to the capturing phase, a phase of stirring the mixture contained in the pipette cone by applying at least one cycle of suction and discharge of said mixture in the pipette cone. Because of the geometry of the cone, which is tubular in shape, it is possible to obtain a high volume throughput relative to the cross section of the cone, and consequently efficient stirring. Furthermore, high turbulences exist in the cone that are naturally generated by the flow of the liquid, said turbulences increasing the efficiency of the stirring. Advantageously, a disposable accessory is provided in the cone for increasing this effect.

According to one embodiment, the method comprises, prior to the transferring phase, at least one phase of washing the particles captured on the internal wall of the pipette cone by:
  deactivating the magnetic field;
  releasing the captured particles by applying, from a well containing a washing solution, at least one cycle of suction and discharge of the washing solution in the pipette cone;
  applying a second phase of capturing on an internal wall of the pipette cone:
    by applying the first magnetic field to the pipette cone, and by applying at least one cycle of suction and discharge of the mixture contained in the pipette cone in the well containing the washing solution.

According to one embodiment, the release of the captured particles comprises a phase of applying the cycles in such a way as to carry out an up and down movement of a meniscus of said solution over a pellet of particles captured in the pipette cone, said up and down movement of said meniscus being carried out on a portion of the cone less than the total length of the pipette cone.

More particularly, the release of the captured particles comprises a second phase of applying the cycles in such a way as to totally suction and discharge the cone washing solution. The frequency of application of the cycles of the second phase is lower than the frequency of application of the cycles of the first phase.

In particular, prior to the release of the captured particles, the method comprises at least two washing phases carried out in two distinct washing solutions.

This embodiment is particularly advantageous when the components contained in the biological sample are nucleic acids (e.g. DNA, RNA).

According to another embodiment, the components contained in the biological sample are microorganisms (e.g. bacteria, fungi, yeasts), and the method comprises a single capturing phase and a single washing phase.

In particular, the mixture of the sample with the magnetic particles has a volume of greater than 1 milliliter, and preferably greater than or equal to 2 milliliters, and the volume of the recovery well is less than or equal to 200 microliters, and preferably less than or equal to 100 microliters.

According to one embodiment, the method comprises, prior to the transferring phase, at least one phase of washing the particles captured on the internal wall of the pipette cone:
  by suctioning the washing solution in said pipette cone;
  then by modulating the first magnetic field applied to the magnetic particles in order to capture said particles on the internal wall of the pipette cone;
  then by discharging the pipette cone washing liquid.

In other words, the modulation of the magnetic field induces a reorganization of the pellet of particles captured on the wall of the cone. In particular, the pellet can change shape, or can spread, slip or else "roll" on the wall of the pipette cone. This reorganization of the pellet makes it possible to further increase the efficiency of the washing, this being all the more since this reorganization can be carried out together with cycles of suction and discharge of the washing solution.

In particular, the modulation of the first magnetic field is carried out:
by moving the pipette cone parallel to a longitudinal axis of said cone, and by keeping the first magnetic field constant;
and/or by passing magnets spaced out from one another in front of the captured particles.

In other words, the modulation is obtained simply, for example by a technician who slides a strip of magnets or by an automated device which applies a simple mechanism of translational movement of a strip of magnets.

According to one embodiment, the volume of the pipette cone is at least ten times greater than the volume of the recovery well. According to one embodiment, the volume of the mixture is at least three times greater than the volume of the pipette cone.

According to one embodiment, the components belong to the group formed by single-stranded or double-stranded nucleic acids (DNA and/or RNA), microorganisms, proteins and peptides. The components consist of any other type of molecules depending on the functionalization given to the magnetic particles.

The aim of the present invention is also to provide a device for carrying out the method which has just been described, which is not very bulky and which is simple for a laboratory technician to use.

To this effect, a subject of the invention is also a pipette holder comprising:
a base;
a recess made in the base, which can removably house a well support;
a pipette support comprising a first housing into which can be, advantageously removably, inserted a pipette equipped with at least one tubular pipette cone comprising a tip intended for pipetting liquid, the first housing opening out onto the recess of the base, the pipette support being translationally mobile relative to the base in a direction parallel to an axis of the pipette cones and mobile between a first position in which the tip of each pipette cone is inserted in a well of the well support and at least one second position in which said tip is outside said well;
a second housing which can removably house a magnetized part, the second housing facing each of the pipette cones in a position above the tip thereof when the pipette support is in the first position, and the second housing facing the tip of the pipette cone when the pipette support is in the second position.

In other words, the pipette holder receives a pipette and the technician carries out the steps of the extraction method by raising/lowering the pipette, in particular to cause migration of the particle pellet in the tip of the pipette cone(s), by introducing wells (in the form of a plate, a strip, etc.) into the base, and by actuating the pipette.

The pipette holder, which is not very bulky and is transportable, also allows semi-automation of the extraction method when an electronic pipette is used. Such a pipette in fact comprises circuits for suction and discharge in each pipette cone equipping it, and a microprocessor-based electronic circuit. This electronic circuit controls the suction/discharge circuits as a function of setpoints entered by the technician by means of an interface equipping the pipette and/or of a computer/tablet/smartphone connected to the pipette (e.g. by a wireless connection of Bluetooth type), etc. These setpoints consist for example of suction/discharge cycle instructions and/or of a choice of a particular protocol prerecorded in the pipette.

Since the electronic pipette is programmable, a great deal of polyvalence is also obtained in the definition of the extraction method, which can be adjusted as a function of a desired particular magnetic capture (e.g.: nucleic acid purification, magnetic immunoconcentration, etc.). In particular, a protocol suitable for the intended extraction can be recorded in the pipette, the protocol being defined in terms of number of suction and discharge cycles, of cycle sequence, of cycle frequency, of time between the cycles, defined volumes, etc. An autonomous and semi-automated system is thus obtained.

Finally, the pipette cones are detachable from the pipette, and therefore easily replaceable, without the pipette being taken out of service for a long period of time.

According to one embodiment, the first housing comprises an opening for the frontal insertion of the pipette into and the frontal removal of the pipette from the first housing of the pipette support. The frontal insertion and removal of the pipette and of the cones in position minimize the risk of touching the pipette holder with the cone tips, and therefore the risk of contamination of the pipette holder.

According to one embodiment, the second housing is made in the base.

In particular, the pipette support comprises a third housing into which the magnetized part can be removably inserted in order to face each pipette cone at a position above the tip of said cone when the pipette support is in the second position.

In other words, when the magnetized part (e.g. comprising one or more permanent magnets) is present in the third housing, it is rigidly linked to the pipette cones and therefore follows their translational movement relative to the base. During such movements, the magnetized part therefore keeps the pellets of magnetic particles attached in the cones. The technician can thus for example raise the pipette in order to more easily move a well support in the base without the risk of moving the particle pellets in the cones.

According to one particular embodiment, the second and third housings communicate, and the pipette support comprises means capable of removably maintaining the magnetized part in the third housing. In this way, the technician can detach the magnetized part from the pipette support which then automatically takes a place in the base by falling into the second housing. This detachment takes place in particular for the operation of migration of the magnetic particles in the cone tips.

According to one embodiment:
the base comprises at least one toothed wheel which can rotate;
and the pipette support comprises a rack which engages with the toothed wheel in order to translationally move the pipette support relative to the base during the rotation of the toothed wheel.

In particular, the pipette holder comprises a device for locking and unlocking the pipette support in the first position. In particular, the pipette holder comprises at least one handle that is rigidly connected to the toothed wheel so as to turn said wheel and that is capable of removably attaching to a handle that is rigidly connected to the toothed wheel of another pipette holder, which therefore makes it possible to increase the number of pipette cones during the extraction method.

The subject of the invention is also a system for extracting components contained in a biological sample in liquid form, said components being capable of binding to magnetic particles, the system comprising:
  a pipette equipped with at least one tubular pipette cone comprising a tip intended for pipetting liquid and with a circuit for suction and discharge in each pipette cone;
  at least one well support;
  a pipette holder comprising:
    a base;
    a recess made in the base, which can removably receive each well support;
    a pipette support comprising a first housing into which the pipette is inserted, advantageously removably, the first housing opening out onto the recess of the base, the pipette support being translationally mobile relative to the base in a direction parallel to an axis of the pipette cones and mobile between a first position in which the tip of each pipette cone is inserted in a well of the well support and at least one second position in which said tip is outside said well;
    a second housing facing each of the pipette cones in a position above the tip thereof when the pipette support is in the first position and the second housing facing the tip of the pipette cone when the pipette support is in the second position; and
  a magnetized part removably inserted in the second housing.

In particular, the pipette holder is in accordance with the pipette holder described above.

An aim of the invention is also to provide a well support for the migration of magnetic particles from the tips of pipette cones into recovery wells.

To this effect, a subject of the invention is also a well support, comprising a part in which recesses for receiving the wells are made, and at least one magnet facing each of the recesses made in said part.

BRIEF DESCRIPTION OF THE FIGURES

The invention will be understood more clearly on reading the description which follows, given solely by way of example, and made in relation to the appended drawings, in which identical references denote identical elements, and in which:

FIG. 7 is a face-on view of a magnetized part according to the invention;

FIG. 9 is a photograph of the pipette cones of a system according to the invention with pellets of magnetic particles placed approximately halfway up the cones;

FIG. 10 is a photograph of these same cones with the pellets placed in the tips of said cones;

FIG. 11 is a photograph of PCR elution tubes in which the magnetic particles have been recovered;

FIGS. 12A, 12B, and 12C illustrate a second embodiment of the pipette holder according to the invention;

FIGS. 13A, 13B, and 13C further illustrate the second embodiment of the pipette holder;

Figure 15:
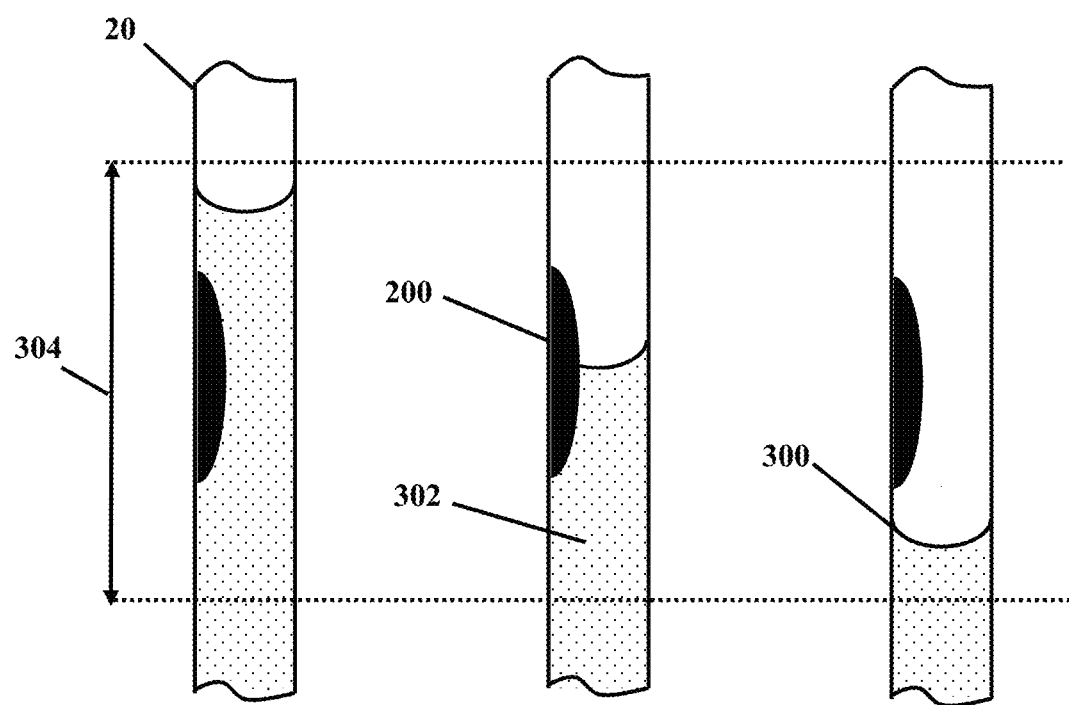
FIG. 15 is a diagrammatic view illustrating the up and down movement of a meniscus of a solution on a pellet of particles for detaching said pellet from the wall of a pipette cone.

Except for FIG. 15, the description is given in relation to planes and photographs on a reduced scale of an actual system.

DETAILED DESCRIPTION OF THE INVENTION

With reference to FIGS. 1 to 7, a system 10 for extracting (FIG. 1) components contained in a liquid sample comprises an electronic pipette 12 (FIG. 2), a pipette holder 14 (FIG. 3) into which the pipette 12 is inserted, one or more well supports 18a, 18b (FIGS. 5 and 6) which can each be inserted into the pipette holder 14, and a first magnetized part 16 (FIG. 7).

Figure 2A:
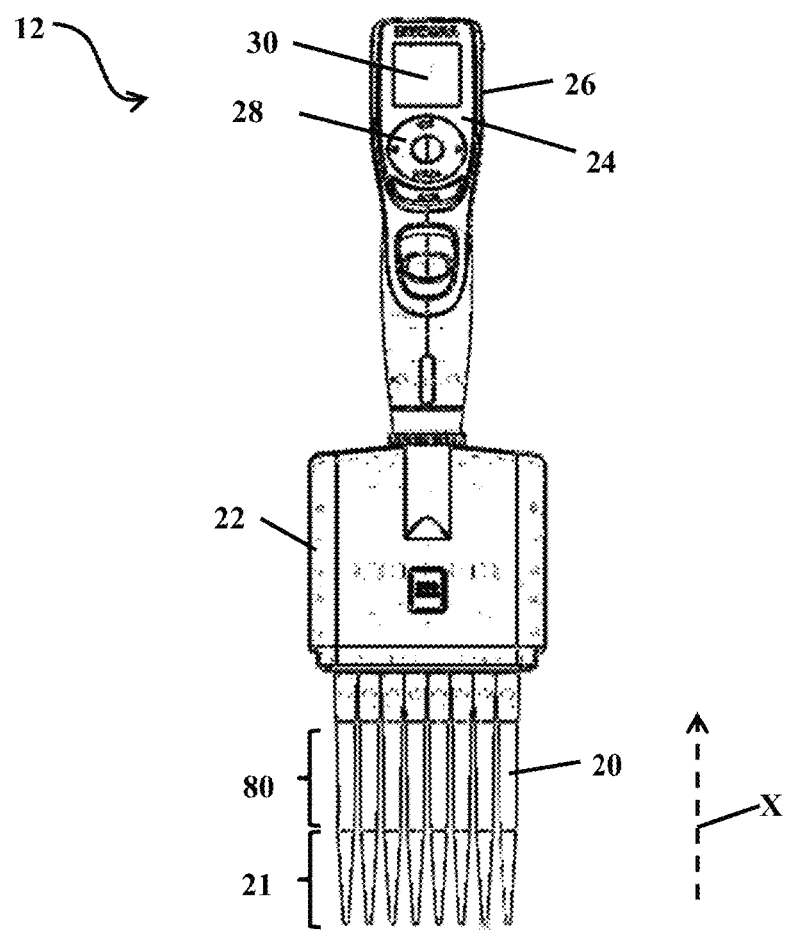
FIGS. 2A and 2B are face-on perspective views of an electronic pipette and of the removable pipette cones thereof.

The pipette 12, which is portable, comprises a row of pipette cones 20, and a body 22 on which the cones 20 are mounted (FIG. 2A). This body 20 houses a circuit for suction/discharge of liquid in the cones 20 (for example a set of pistons actuated by an electric motor), and an electronic circuit for controlling the suction/discharge circuit. The electronic circuit, which comprises for example a microprocessor and one or more computer memories, is programmable, and has, embedded within it, instructions for carrying out one or more pipetting protocols, each protocol comprising one or more steps. The electronic circuit also comprises a man-machine interface 24 housed in a handle 26 of the body 22, the interface comprising a set of selection and navigation buttons 28 and a display screen 30 allowing visualization and selection of various recorded pipetting protocols. The user can in particular program the electronic pipette 12, e.g. by downloading, into said pipette, instructions from a computer connected to the pipette 12 through a wireless link, for example Bluetooth. The user can also select, via the interface 24, a prerecorded protocol. The pipette 12 is moreover capable of suctioning a predefined volume of liquid into each of the cones 20, discharging a predefined volume from each of the cones, and carrying out automatic suction/discharge cycles of variable time and frequency.

Figure 2B:
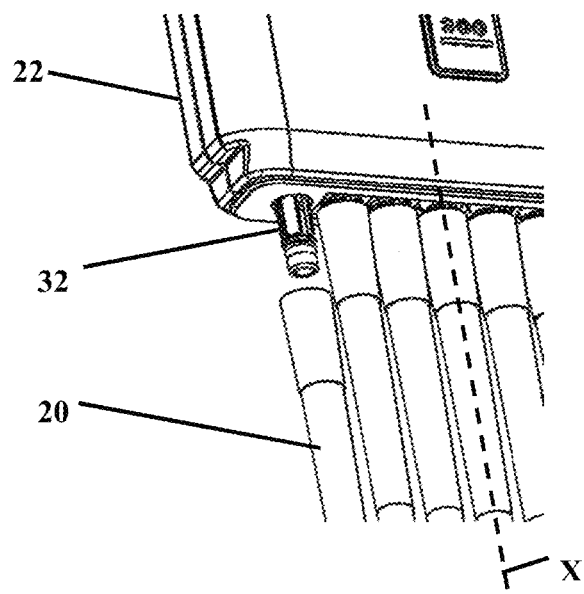
Figure 3A:
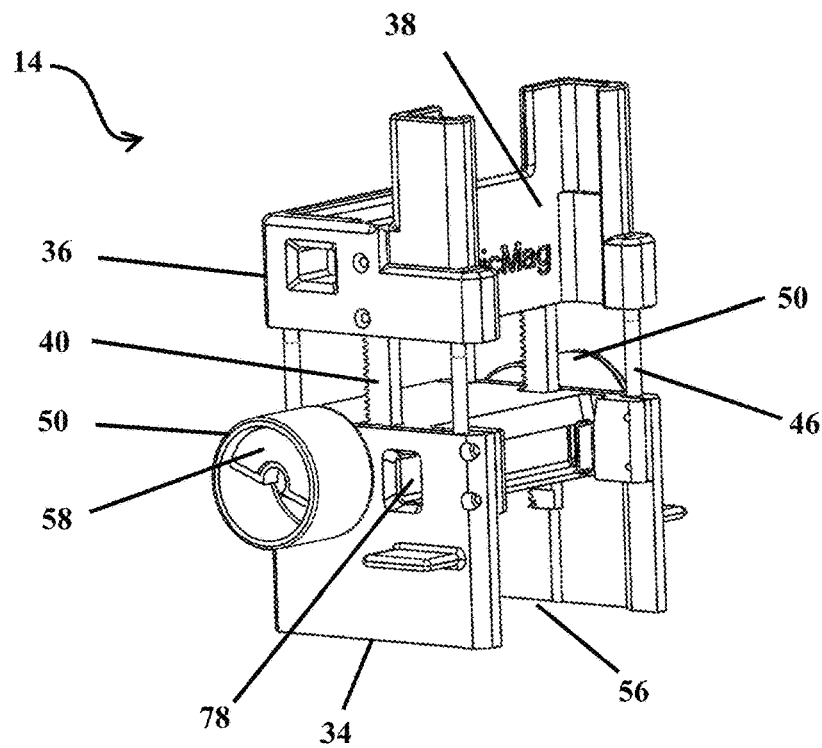
FIGS. 3A and 3B are face-on perspective views of a pipette holder according to the invention.
Figure 3B:
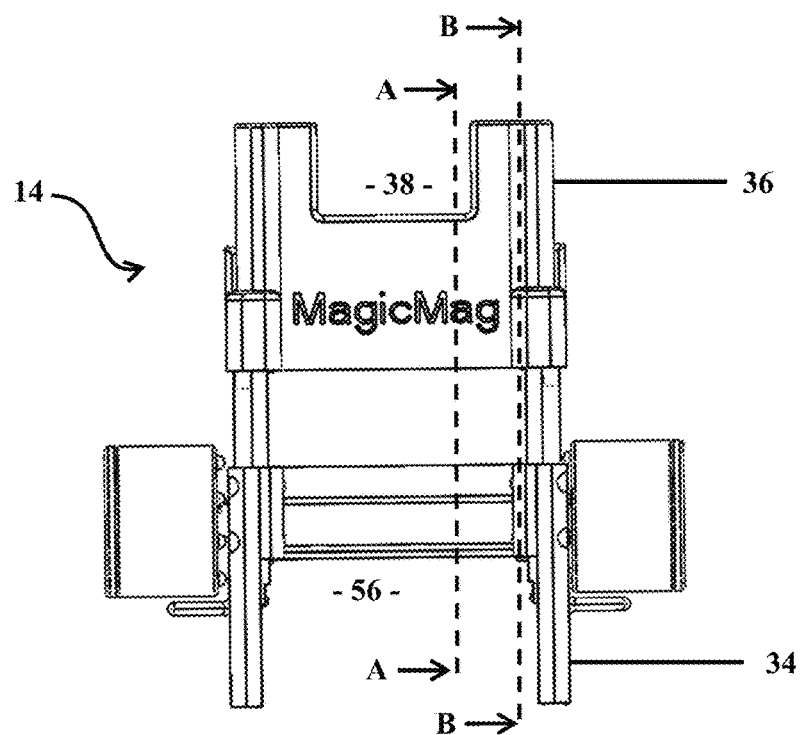

As illustrated more particularly in FIG. 2B, the cones 20, which are tubular in shape and have a longitudinal axis X, are removable by fitting to lugs 32 protruding from the body 22, which allows them to be replaced. The cones consist moreover of a plastic, for example a polypropylene, which has the effect of making them "transparent" to a magnetic field and allows the capture of magnetic particles, as will subsequently be described in greater detail. Finally, each cone 20 has a tapered profile 21, or "tip", at its open pipetting end. This part 21 has a reduced cross section in a plane perpendicular to the axis X, which makes it easier to introduce it into containers or wells, as is known per se.

The electronic pipette 12 is for example the "8-channel Viaflo II" model sold by the company ©Integra Biosciences AG, Switzerland, the elements of which model are described in patent applications US 2009/071266, US 2009/074622, US 2011/076205 and US 2008/095671.

Figure 1:
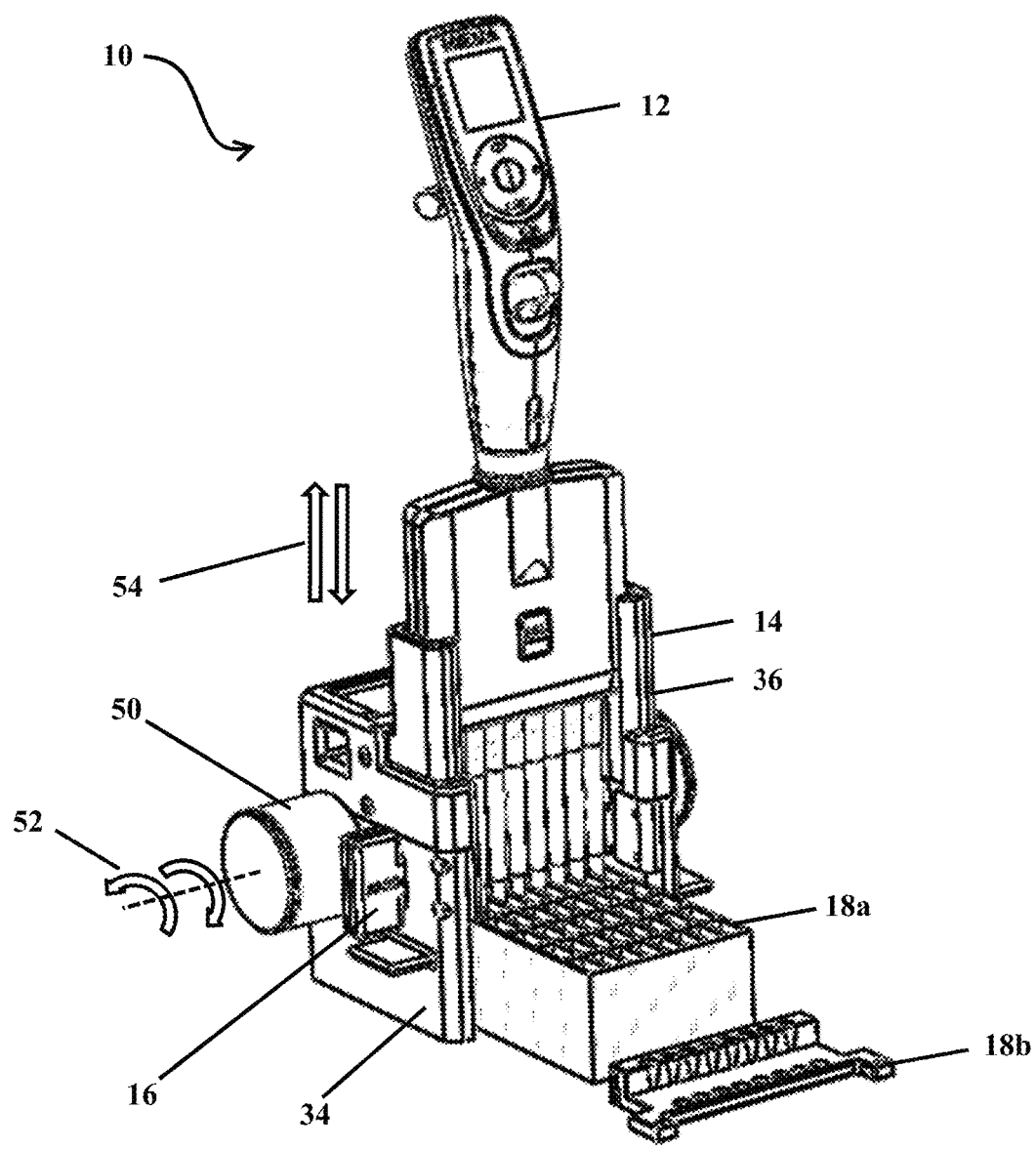
FIG. 1 is a perspective view of an extraction system according to the invention.

The pipette holder 14 for its part comprises (FIGS. 3A and 3B) a base 34, intended to be placed on a workbench (e.g. a laboratory table or bench), and also a mobile part 36 which moves relative to the base 34. The mobile part 36, also called "pipette support", comprises a housing 38 into which the pipette 12 can be removably inserted and kept immobile as illustrated in FIG. 1. For the translational movement of the pipette support 36 relative to the base 34, the support 36 comprises one or more racks 40, for example two of them, which engage with toothed wheels 42 mounted on an axle 44 which rotates and which is inserted in the base 34. One or more rods 46 are also attached to the support 36 (respectively in the base 34) and slide in orifices of the base 34 (respectively in the support 36) in order to guide the support 36 in its translational movement. One or two rotation handles 50 are also attached to the end of the axle 44 in order to allow the user to easily turn the latter in the direction of the arrows 52 (FIG. 1) and therefore cause the pipette support 36 to rise and descend as illustrated by the arrows 54 (FIG. 1). The translational movement of the pipette support 36 relative to the base 34 is thus parallel to the axis X of the cones 20 when the pipette 12 is placed in the housing 38 of the support 36, and therefore parallel to the direction of gravity when the base 34 is placed on a horizontal workbench, such that the support 36 "rises" or "descends".

The base 34 is open on its front face 56 so as to allow the introduction and the removal of the well supports 18a, 18b, thus defining a housing for the latter. This housing is open on its upper part so as to allow the cones 20 of the pipette 12 to reach said well supports when the pipette descends. Thus, as described in greater detail below, the pipette 12 can take up several positions relative to the base 34, and thus relative to a well support 18a, 18b inserted in the latter. In particular, the pipette 12 can take up a position in which the tips 21 of the cones 20 dip into wells of the support 18a, 18b, and at least one position in which the tips 21 do not dip into the wells, and are at a distance from the latter so as to allow the well supports to be handled by the user and magnetic particles to be captured in a central position of the cones 20.

Figure 5:
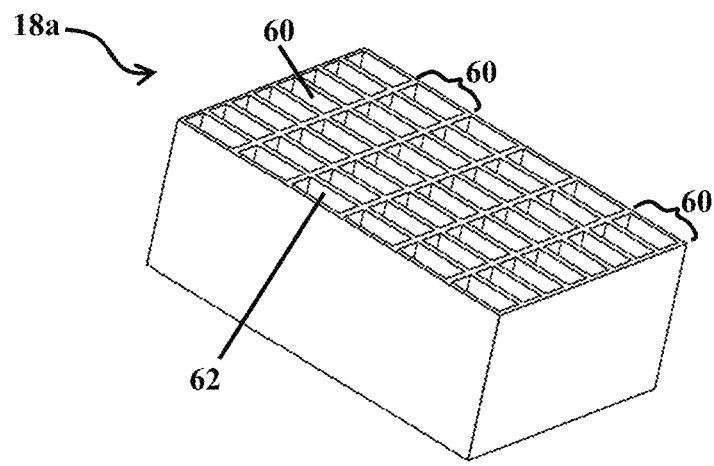
FIG. 5 is a perspective view of a "deepwell" plate comprising wells.

With reference to FIGS. 5 and 6, the well supports can have several forms depending on the desired extraction. In particular, a well support is a compartmentalized plate 18a (FIG. 5), usually called a "microplate" of "DeepWell" type. This type of plate comprises rows 60 of wells 52 into which the row of pipette cones 20 can dip. Each row 60 can thus receive a particular liquid used during the extraction step carried out by the system 10. The passing from one row 60 to the other is then carried out simply by the user who places, in line with the pipette cones 20, the particular row 60 containing the liquid required for the step that has to be carried out.

Figure 6A:
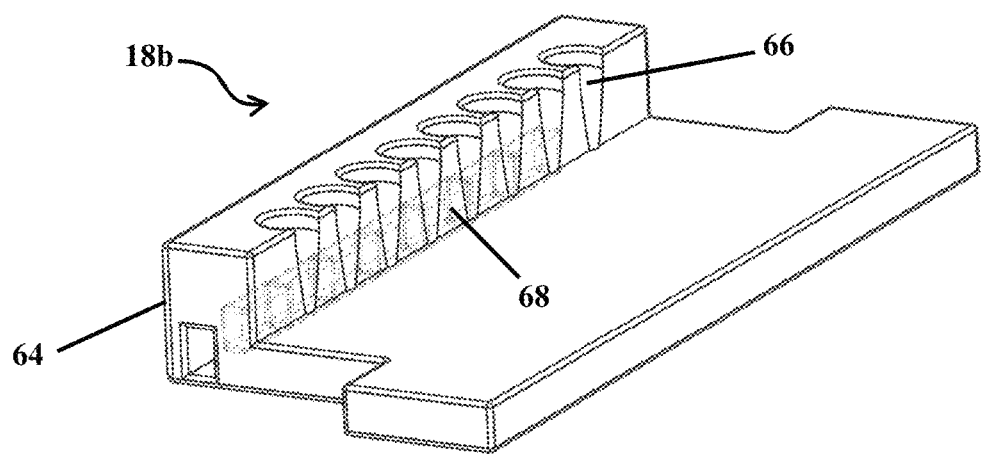
FIGS. 6A and 6B are perspective views of a magnetic rack and of PCR elution tubes that can insert into the rack.
Figure 6B:
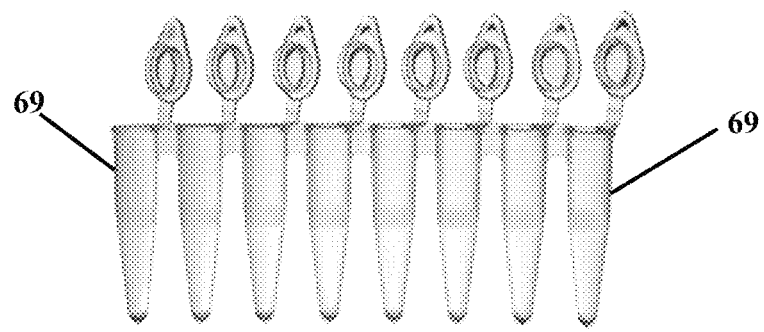

Another well support, described in FIG. 6A, is magnetized and specifically designed for the migration of magnetic particles from the tips 21 of the pipette cones 20 into wells. The support 18b comprises for this purpose a body 64 in which is made a row of housings 66 that can receive the row of pipette cones 20, and in which is inserted a second magnetized part 68 comprising one or more permanent magnets, for example a permanent magnet in proximity to each of the wells 66. The magnetized part 68 is placed under the wells 66 or facing their lower portions as illustrated. Thus, the tips 21 of the pipette cones 20 are placed above the magnetized part 68 when said tips are dipped into the wells 66. Finally, the support 18b serves as a magnetic rack which removably receives tubes 69 in the housings 66, for example PCR elution tubes as illustrated in FIG. 6B, for the purposes for example of subsequent transfer of the extraction product recovered therein.

The first magnetized part 16, the function of which is to capture magnetized particles in the cones 20 in a manner subsequently described in greater detail, comprises, for its part, one or more permanent magnets 72, advantageously a row of permanent magnets separated from one another by spaces 74, and even more advantageously a permanent magnet facing each pipette cone 20 when the part 16 is entirely inserted in the base 34. The part 16 also comprises a handle 76 for better gripping by the user.

A housing 78 for receiving the magnetized part 16 is provided in the base 34, the housing 78 being placed such that the part 16 faces the pipette cones 20 above their tip 21, and preferably faces a central zone 80 at a height greater than the well, when the tips 21 dip into the wells, held in a well support. In this way, the particles are captured in a volume of the cone that is sufficiently large so as not to form plugs in the cones.

Figure 4A:
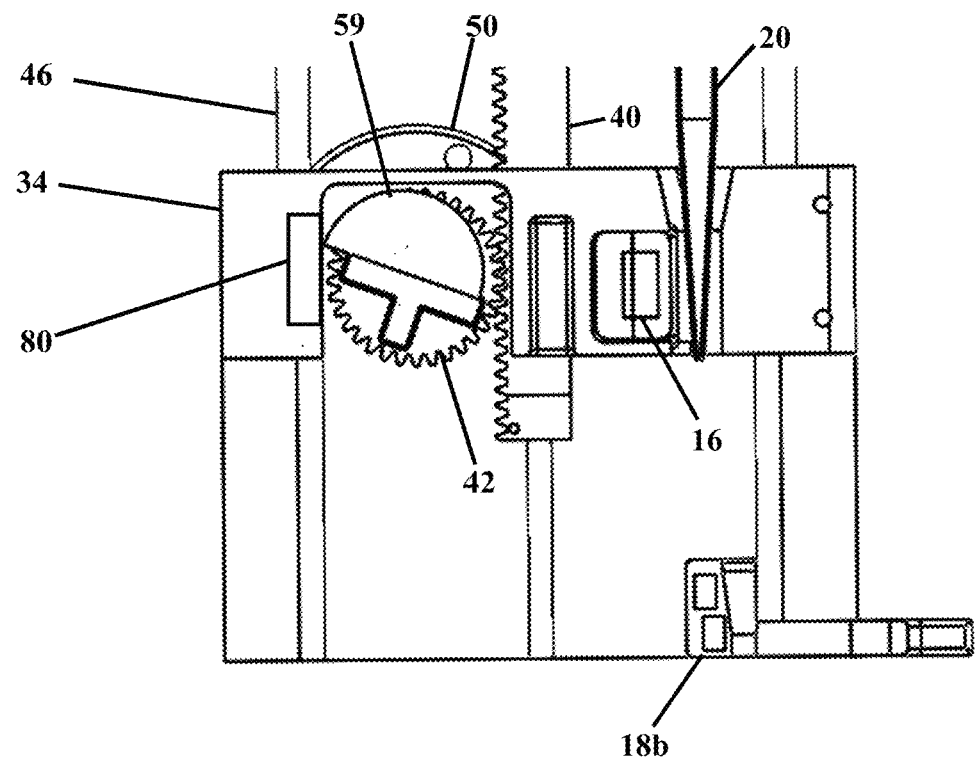
FIGS. 4A and 4B are detailed sectional views of the pipette holder of FIG. 3, respectively along the planes A-A and B-B of FIG. 3B.

The pipette holder 14 also comprises means for controlling the speed at which the support 36 rises. In particular, the rack and the toothed wheel are designed such that half a turn (180°) of the wheel 50 makes it possible to travel across the whole of the rack, and a flyweight 58 integrated into each of the handles 50 in an off-axis manner relative to the axle 44. These flyweights, under their weight and the associated lever effect, generate a rotation couple which rotates the axle 44 while at the same time limiting the couple transmitted by hand by the user. Advantageously, as illustrated in FIG. 4A, a substantial part of the axle 44 is also formed of a semi-cylindrical flyweight for the same purpose. This mechanical assistance helps to raise the pipette support, and therefore limits musculoskeletal problems, and carries out braking which allows the user to more accurately control the speed at which the support 36 rises and descends.

Other mechanisms for controlling the speed of the support 36 can be provided for, in particular magnetic braking. For example, with reference to FIG. 4A, the flyweight 59 comprises a magnetizable material (e.g. steel or equivalent) and a third magnetized part 80 (parallelepipedal or in the shape of an arc of a circle concentric to the axle 44) is housed in the base 34, preferably facing the magnetized part 16 with respect to the axle 44 so as not to disrupt the extraction. When the flyweight 59 of the axle passes in front of the magnetized part 80, the rotational movement of the axle 44 is slowed because of the braking couple generated. This makes it possible, on the one hand, to compensate for the effort for raising the pipette during the rise (by acting as assistance for the user) and, on the other hand, to control the speed at which the pipette rises when it is desired to cause the magnetic particles to descend to the bottom of the pipette cones, as will be described below.

Figure 4B:
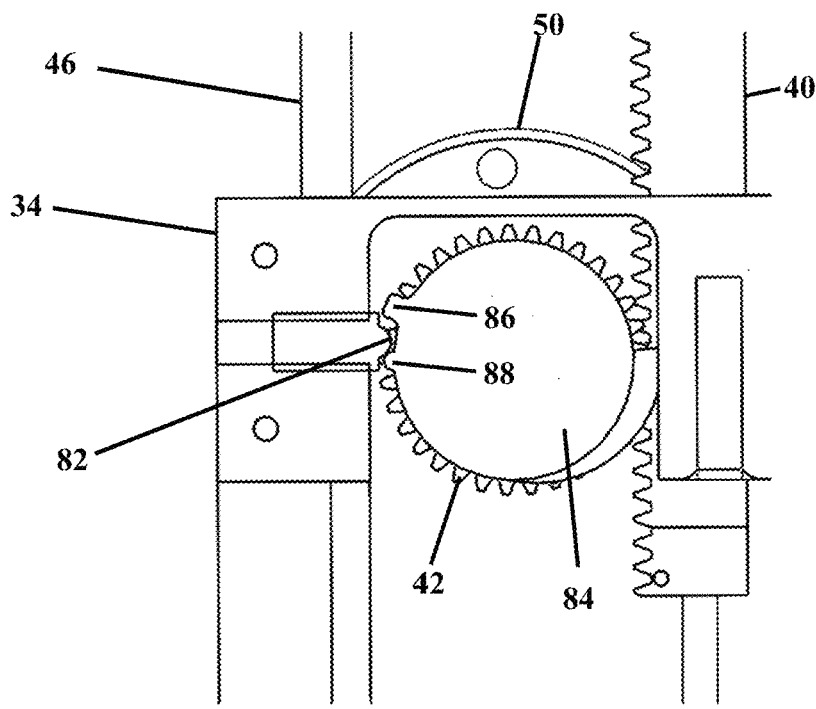

A stop mechanism is also advantageously provided for, as illustrated in FIG. 4B. In this variant, a wheel 84 made of deformable material (e.g. of elastomer) is mounted on the axle 44 and comprises two teeth 86, 88. A protuberance 82, for example a hemispherical protuberance, moreover protrudes from the base 84 facing the wheel 84. When the user raises the pipette 12 by actuating the wheel 50, the first tooth 86 encounters the protuberance 82. When the cut applied to the wheel 50 is increased, the tooth 86 bends, passes the protuberance 82, and returns to its shape. In this position, the tooth 86 can then rest on the protuberance 82, the hardness of this tooth being chosen such that it does not bend under the action of the weight of the pipette 12 and of the pipette holder 36. The pipette is thus blocked in the top position, the user thus being able to release the wheel 50. The second tooth 88, which is larger in dimension (e.g. length and/or width) requires a much greater couple in order for it to pass, and thus defines a stop for preventing the pipette holder 36 from disconnecting from the base 34, unless the user deploys a force capable of breaking this tooth. As a variant, the protuberance 82 is replaced by a stop comprising a ball mounted on a spring in a housing of the base. The wheel 84 can thus be made of a hard material. The action of the first tooth 86 then has the effect of pushing the ball into its housing, thus allowing the tooth 86 to pass.

Figure 8:
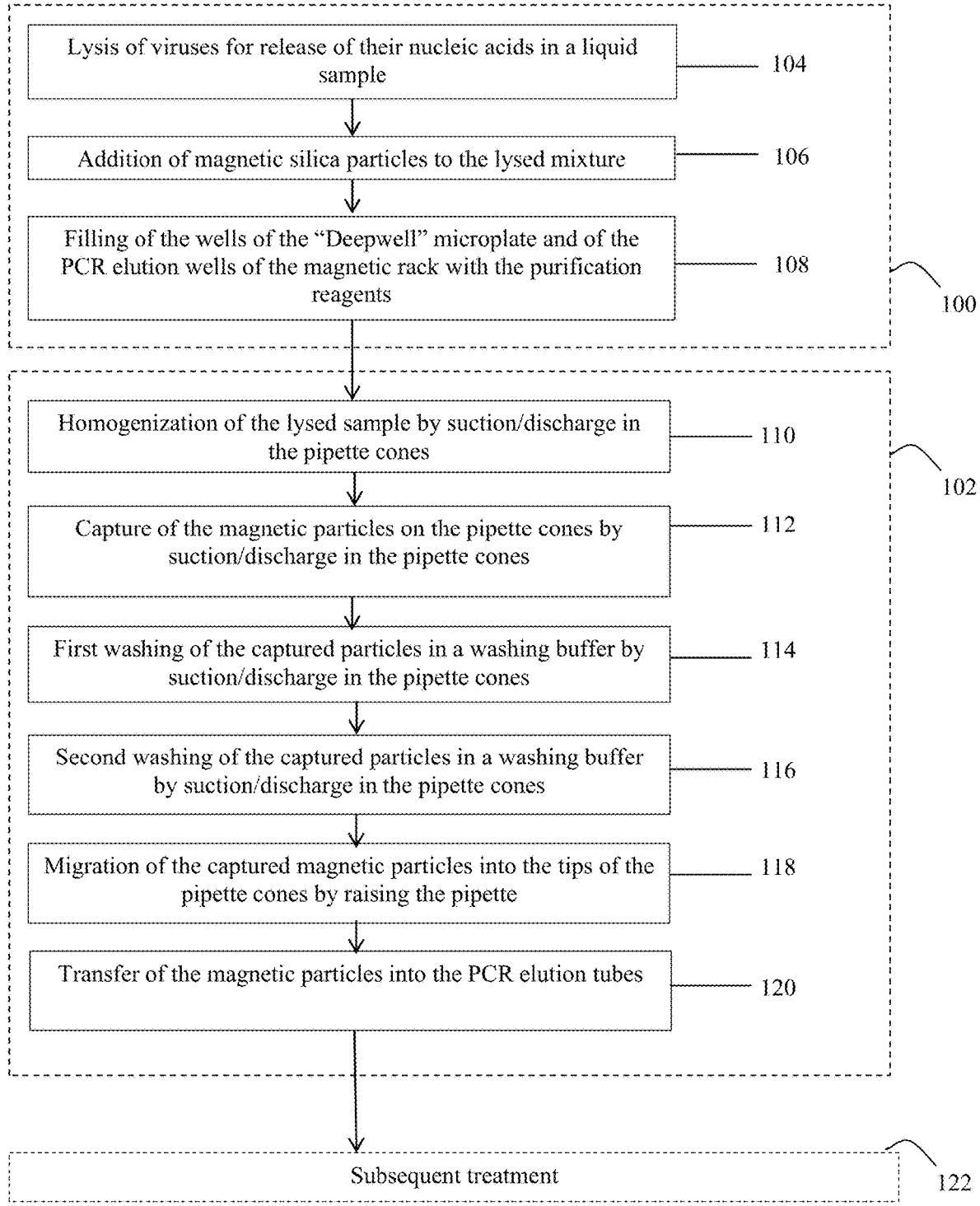
FIG. 8 is a flowchart of an extraction method according to the invention.

Presently described is a method for extracting components contained in a liquid sample by means of magnetic particles, this method being carried out by means of the system which has just been described. The method is based on the combination of the pipette holder, the programmable electronic pipette and pipette cones (e.g. with a volume of 1250 μl) in order to carry out the various steps of capturing, washing and eluting magnetic particles for treating a sample volume per pipette cone of between 1 ml and 5 ml. The capture of the magnetic particles is carried out sequentially in the pipette cones during suction/discharge cycles on all of the volume of the sample to be treated. By way of example, a method for purifying viral nucleic acids using NucliSENS© chemistry, namely an extraction of nucleic acids by means of magnetic silica particles, is described in relation to the flowchart of FIG. 8.

The method begins with a step 100 of preparing the various samples and reagents required for the purification, followed by said purification in 102.

In particular, the preparation 100 consists, in 104, in mixing the biological sample comprising viruses from which it is desired to extract the nucleic acids, with a reagent for chemical lysis of viruses (e.g. the "Nuclisens miniMAG" lysis reagent from bioMérieux, reference 200292, or the "Nuclisens easyMAG" lysis reagent from bioMérieux, reference 280130), in a proportion of two volumes of lysis reagent for one volume of sample. The mixture is then heated for 30 minutes at 56° C., thus releasing the nucleic acids from the viruses in a manner known per se. Magnetic silica particles (e.g. particles having a paramagnetic, ferromagnetic or ferrimagnetic core which may or may not exhibit remanence, said core being covered with a silica shell), having the property of binding with nucleic acids, are then introduced, in 106, into the lysed sample.

The preparation 100 continues, in 108, by filling the microplate 18a, having wells 62 of 5 ml, and the PCR elution tubes 69 of 0.2 ml of the magnetic rack 18b such that:

each well of the first row of the microplate 18a is filled with the lysed sample comprising the silica particles, hereinafter the "lysed sample". The total volume in each well of the first row is preferably greater than 1.5 ml because of the use of the 5 ml Deepwell microplate and of the volumes handled by the electronic pipette;

each well 66 of the second row of the microplate 18a is filled with 1250 μl of washing buffer (e.g. the "NucliSENS easyMAG Extraction Buffer No. 2" from bioMérieux, bMx reference 280131);

each well 66 of the third row of the microplate 18a is filled with 1250 μl of washing buffer (e.g. the "NucliSENS easyMAG Extraction Buffer No. 2" from bioMérieux, bMx reference 280131);

each PCR elution tube 69 inserted in the magnetic rack 18b is filled with a volume of 100 μl of elution buffer (e.g. the "NucliSENS easyMAG Extraction Buffer No. 3" from bioMérieux, reference 280132).

The user then places:

the electronic pipette 12, with its row of cones 20, in the housing 38 of the pipette holder 14 in a raised position so as to allow the introduction of the plate 18a; and the plate 18a in the housing 56 of the base 34 with the first row of wells comprising the lysed sample in line with the cones 20.

The extraction 102 begins with the homogenization of the lysed sample. To do this, the magnetized part 16 is not placed in the base 34 and does not therefore interfere with the cones 20. The user turns one of the wheels 50 so as to dip the tips 21 of the cones 20 in the row of wells of the plate 18a comprising the lysed sample. The user then selects, by means of the interface 24 of the pipette 12, a first pipetting protocol comprising at least one phase of suction/discharge of the lysed sample in the cones 20, and launches the protocol selected. These phases (e.g. two of them) each comprise at least one suction/discharge cycle (e.g. five cycles), followed by a waiting period of several minutes, for example 5 minutes. For the purposes of the invention, a suction and discharge cycle consists in filling at least three quarters of, for example completely filling, the cones and then in completely emptying them, unless specified otherwise by the program.

Once the homogenization is finished, the cones 20 are empty and their tips 21 dip into the wells containing the lysed sample. The purification 102 continues with the capture, in 112, of the silica particles, of the lysed sample, on the internal wall of the cones 20. To this effect, the user places the magnetized part 16 in the housing 78 of the base 34, selects, by means of the interface 24 of the pipette 12, a second pipetting protocol and then launches the protocol selected. The second protocol comprises a plurality of suction/wait/discharge cycles, e.g. about ten cycles, a suctioning operation being separated from a discharge operation by a few seconds, e.g. about ten seconds. At each suctioning operation and each discharge operation, a part of the particles contained in the lysed sample is captured on the wall of the pipette cones by virtue of the magnetic field produced by the magnetized part 16. The magnetic particles, and therefore also their bound nucleic acids, are thus captured in the form of pellets of particles 100 facing the magnetized part 16, and preferably on a central zone halfway up the cones 20, as illustrated in FIG. 9.

Once the capture has finished, the lysed sample having been completely discharged from the cones 20 and the magnetized part 16 still being in position, the purification 102 continues with a first washing step 114. To this end, the user raises the pipette holder 14 (respectively raises the pipette 12) so as to release the plate 18a from the cones 20, aligns the second row of the plate 18a with the row of cones 20, then repositions the pipette holder (respectively descends the pipette) so as to dip the tips 21 of the cones in the wells of the plate 18a. The user then selects, by means of the interface 24, a third pipetting protocol comprising at least one phase of suction/discharge of the lysed sample in the cones 20, then launches the protocol selected. The third protocol is for example identical to the first protocol. The repeated passing of the washing buffer over the particle pellets thus makes it possible to wash said particles. This washing step is advantageously completed, or carried out jointly, with a modulation of the magnetic field capturing the particles on the cones. For example, the user raises and descends the pipette 12, which has the effect of moving the particle pellets on the cones, or alternatively the magnetized part 16 comprises a set of permanent magnets and the user slides the magnetized part 16, in an up and down movement, from its housing 78, such that the intensity and the lines of magnetic fields capturing the pellets vary, while at the same time maintaining the particles captured on the cones. The modulation of the magnetic field thus has the effect of reorganizing the pellets during the washing, and increasing the efficiency thereof.

A second washing operation is then carried out in 116 by means of the washing buffer of the third row of the plate 18*a*. For example, the first washing buffer is completely emptied out of the cones, then a second washing operation identical to the first washing operation is carried out.

Subsequent to this second washing operation, a step of migration 118 of the particle pellets 200 into the tips 21 of the cones 20 is carried out. To do this, the cones 20 preferentially remain filled with the second washing buffer in order to facilitate the slide of the pellets 200 and remain aligned with the second row of the plate 18*a*. The user then turns one of the wheels 50 so as to raise the pipette 12. Since the magnetized part 16 is rigidly connected to the base 34, the pellets thus remain immobile relative to said part and migrate toward the tips 21 by sliding along the walls of the cones 20 as the pipette is raised. The user stops the raising of the pipette 12 once the pellets 200 are in the tips 21, as illustrated in FIG. 10, at an average distance of a few millimeters, e.g. 8 mm, from the open ends of the cones. In this position, the user selects and then launches, by means of the interface 24, the discharge of the washing buffer contained in the cones 20 into the wells of the plate 18*a*. Optionally, one of the washing phases, or an additional washing phase, consists in removing the magnetized part so as to release the magnetic particles and to carrying out a washing operation while at the same time stirring the particles in the washing solution by means of suction and discharge cycles. The particles are then captured once again by repositioning the magnetized part and by performing suction and discharge cycles as previously described.

The purification 102 ends with a step 120 of transferring the magnetic particles present in the tips 21 of the cones 20 into the PCR elution tubes 69. To this effect, the user raises the pipette holder 14, removes the plate 18*a*, places the magnetic rack 18*b* in the housing 56 so as to align the PCR tubes 69 with the row of cones 20, rests the pipette holder 14 and removes the magnetized part 16 from the base 14 in order to release the captured magnetic particles from the cones. Once the tips 21 have been dipped into the tubes 69, the user selects, by means of the interface 24, a fourth pipetting protocol, then launches the protocol selected. A first variant of this protocol consists of cycles of suction and discharge of the elution buffer in the tips 21 of the cones 20, which makes it possible to resuspend the magnetic particles by breaking up the particle pellets. Moreover, the frequency chosen for the cycles makes it possible, at each discharge in the tubes 69, for some of the magnetic particles to be captured in the tubes 69 by virtue of the magnetic field of the magnetized part 68 inserted in the rack 64. Furthermore, these cycles make it possible to "rinse" the tips 21 in order to recover particles adhering to the walls of the cones. In a second variant of the protocol, suction and discharge cycles are first of all carried out at a higher frequency so as to stir the buffer and the particles more vigorously, and therefore to obtain accelerated homogenization facilitating the transfer into the elution tubes 69. The transferring step ends with the complete discharge of the elution buffer in the tubes 69.

Under the effect of the magnetic field of the rack 64, the magnetic particles are then definitively separated from the elution buffer, as illustrated in FIG. 11. The user can thus recover the tubes 69 for a subsequent treatment, in particular the elution of the nucleic acids by heating, in a manner known per se.

In the embodiment of the pipette holder previously described, the magnetized part 16 is inserted in the base 34. Thus, when the user wishes to move the plate 18*a* forward, he can raise the pipette sufficiently high to perform this operation. This causes, as for the migration of the particles to the tips, the pellets 200 to move over the walls of the cones 20, which has the advantage of "reorganizing" the pellets which can roll over on themselves. The efficiency of the washing is thus thereby reinforced. On the other hand, this means that the user takes care not to ever raise the pipette too far, so as not to cause the pellets to leave the cones. To do this, the user can for example raise or tilt the pipette holder so as to keep the pellets at a distance from the cone openings. This option, which requires repeated raising of a device, the weight of which can be considerable, can however lead in the long term to musculoskeletal problems. In addition, the user must also take care not to raise the pipette holder too much, so that the pellets do not leave the cones.

Figure 12A:
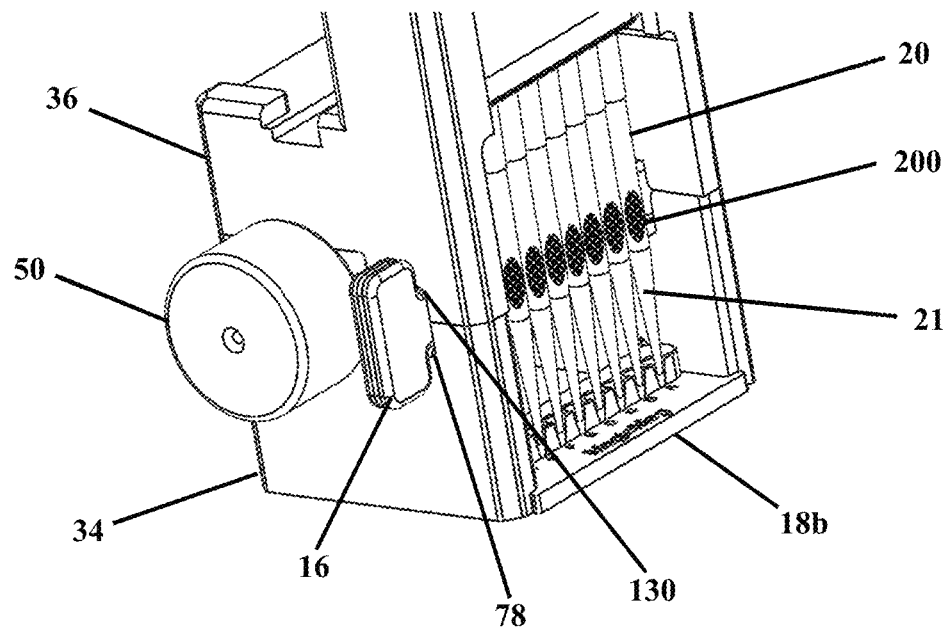
Figure 12B:
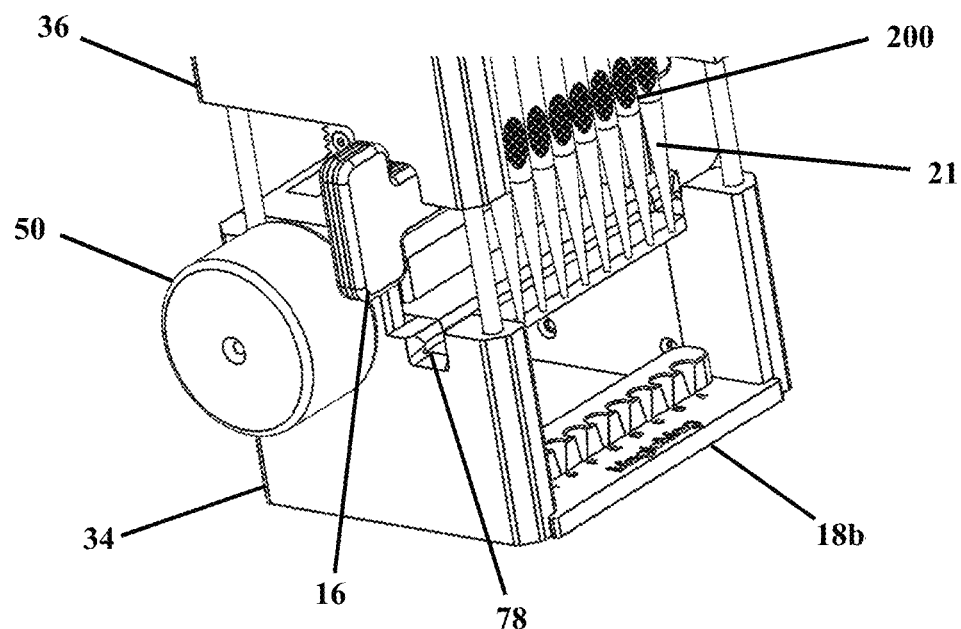

A second embodiment of the pipette holder according to the invention allows the handling of the plates 18*a*, 18*b* by raising only the pipette, and therefore avoiding raising the pipette holder 14, while at the same time guaranteeing that the particle pellets remain at a distance from the tips 21 of the cones. This second embodiment, and also the variations generated regarding the method which has just been described, are illustrated in FIGS. 12 and 13.

More particularly, the second embodiment differs from the first embodiment by virtue of the means of receiving the magnetized part 16 in the pipette holder 14. In particular, the base 34 comprises the housing 78 for the insertion and removal of the magnetized part 16 as previously described and the housing 78 is open in its upper part 130 so as to also allow the insertion and removal of the part 16 vertically in the housing 78. The pipette support 36 also comprises means for attaching the magnetized part 16 in line with the open housing 78, in particular one or more blocks 132 made of magnetizable material (e.g. made of steel) attached to a rear wall 134 of the mobile pipette support 36 (FIG. 12C). In this way, the magnetized part 16 is rigidly connected to the mobile support 36 and remains facing the cones 20 when the user raises and descends the pipette (in particular during the washing phases), as illustrated in FIGS. 12B to 13A.

In order to carry out the migration of the pellets 200 into the tips of the cones 20, the user disconnects the magnetized part 16 from the pipette support 36, by applying a simple downward pressure on the handle 78 of the part 16, and raises the pipette 12. The magnetized part 16 detaches from the blocks 134, thus remains in the housing 78 of the base and is therefore rigidly connected to the base 34, inducing migration of the pellets 200 into the tips 21 of the cones as previously described (FIGS. 13A and 13B). Once the pipette has been raised, the user replaces the plate 18*a* with the rack 18*b* equipped with the PCR elution tubes, removes the magnetized part 16 and redescends the pipette (FIG. 13C, tubes 69 not represented). As a variant, the pipette support 36 can comprise a housing similar to the housing 78 of the base in which the user slides the magnetized part, in particular for the washing phases.

A particular extraction method has been described. However, the present invention applies to any type of capture of magnetic particles and to any type of pipetting sequence. Likewise, a pipette having 8 channels with a particular volume has been described. The pipette can comprise any number of channels of any volume depending on the intended application.

Figure 14:
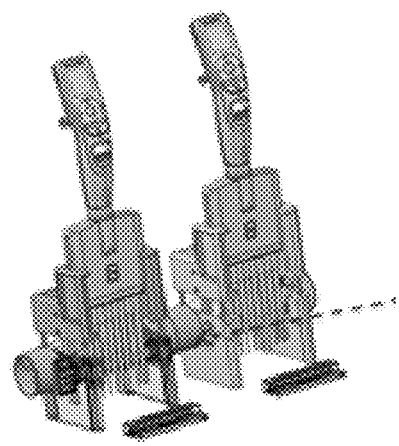
FIG. 14 is a perspective view of two systems of FIG. 1, coupled to the rotation handle means.

In order to increase the number of samples processed, two extraction systems according to the invention can be coupled, as illustrated in FIG. 14. For example, the rotation handles 50 can fit together such that two extractions can be carried out simultaneously, the user raising and descending the pipettes 12 at the same time. To this end, the pipettes can also be synchronized, one pipette controlling, for example, the other pipette.

Likewise, a portable and semi-automated extraction system, particularly suitable for test laboratories having a limited number of extractions to be carried out daily, has been described. However, the invention can be automated. For example, the pipette is integrated into an automated device which comprises programmable mechanisms for raising and descending the pipette and for moving the magnet (or for activating/deactivating electromagnets).

Two washing operations in the wells of the second row and of the third row of the microplate 18a have been described. However, there can be any number of washing operations. Likewise, a single step of capturing the particles in the cones has been described. One or more steps of releasing the particles, each followed by a further capture step, can also be provided for.

In order to release the particles, the magnetic field for capturing the particles is deactivated by removing the magnetized part 16 from its housing, then cycles of suction/discharge of a buffer are carried out in the pipette cones so as to detach the particle pellets from the walls of the cones and to disaggregate them. Such a procedure takes more than 10 minutes to completely detach the pellets from the walls of the cones with a suction/discharge frequency (complete suction and discharge in the cones) of 5 cycles per minute. With reference to FIG. 15, a faster release of a pellet 200 is obtained by carrying out, on the pellet 200, an up and down movement of the meniscus 300 that the buffer 302 forms in a cone 20. In particular, the suction/discharge cycle is regulated such that the meniscus 300 travels a limited path 304 on either side of the pellet 200 in order to increase the frequency with which the meniscus passes over the pellet. Likewise, the frequency of the suction/discharge cycles is increased in order to further increase said frequency of passage, in particular a cycle frequency greater than 2 cycles per second on the zone where the pellet of magnetic particles is present. When this procedure is applied, the pellets detach from the cones in less than 1 minute. The inventors have noted that it is the passing of the meniscus over a pellet which helps to detach the latter. Indeed, tests have been carried out by rapidly stirring the buffer in the cones without passing the menisci over the pellets (i.e. "simple" movement of liquid in front of the pellets) without any notable saving of time. Once the pellet release phase has been carried out, said phase also having the effect of disaggregating the pellets, a phase of stirring by complete suction/discharge in the cones is carried out (e.g. 8 suction/discharge cycles per minute) so as to finish disaggregating the pellets and to homogenize the buffer comprising the particles. These complete suction/discharge cycles in the wells of the microplates stir a greater volume, over a longer path, thereby facilitating the homogenization of the buffer.

A description will now be given of a preferred method for extracting nucleic acids (e.g. DNA and RNA), in particular of viral origin, for example by means of magnetic silica particles. This method comprises a particle release phase, e.g. as previously described, followed by a phase of washing in a buffer and of recapturing the particles. A notable saving of time is obtained, as is an improved extraction. In particular, this method comprises, once the virus lysis step has been carried out:

1. a first step of capturing the magnetic particles in the pipette cones, e.g. in the manner previously described;
2. followed by a first washing step, and preferably by at least one second washing step, in different rows of the microplate that are filled with washing buffer (e.g. the "NucliSENS easyMAG Extraction Buffer No. 1" from bioMérieux, reference 280130). Each washing operation comprises cycles of suction/discharge of the washing buffer with the particles captured on the pipette cones, and lasts at least 15 seconds, preferably between 25 seconds and 35 seconds, for example 30 seconds, and preferably less than one minute;
3. at least one third washing step in a third row of the microplate 18a filled with a washing buffer (e.g. the "NucliSENS easyMAG Extraction Buffer No. 2" from bioMérieux, reference bMx 280131). During this third washing step, the particles are released by removing the magnet, so as to resuspend the particles, the buffer with the particles in suspension being suctioned/discharged in the corresponding wells of the microplate 18a. The third washing step, preferably comprising a phase of passing menisci over the pellets as previously described, lasts a few minutes, in particular 5 minutes;
4. a second step of capturing the particles on the pipette cones, e.g. as previously described;
5. optionally, a fourth washing step, the particles being captured in a third row of the microplate 18a filled with a washing buffer (e.g. the "NucliSENS easyMAG Extraction Buffer No. 2" from bioMérieux, reference bMx 280131);
6. a step of migration of the particle pellets into the tips, followed by a step of transferring into tubes (e.g. comprising an elution buffer, for example the "NucliSENS easyMAG Extraction Buffer No. 3" from bioMérieux, reference 280132), e.g. as previously described.

Washing buffers of the NucliSens range, in particular extraction buffers No. 1, No. 2 and No. 3, have been described. More generally:

- the extraction buffer No. 1 is a buffer which promotes the capture of nucleic acids on silica by creating bridges between the silanol groups of the silica and the phosphate groups of the nucleic acids. It comprises, for example, guanidinium thiocyanate, namely a chaotropic agent as described in the document by R. Boom et al. "Rapid and simple method for purification of nucleic acids." Journal of Clinical Microbiology. 1989; 28 (3): 495-503;
- the first and second washing operations make it possible to remove the residual matrix or microorganism debris,
- the third and fourth washing operations make it possible to remove the traces of GuSCN and of the inhibitors of a PCR-type amplification usually subsequently carried out on the DNA/RNA captured by the magnetic particles,
- the elution buffer included in the PCR cones makes it possible to remove any trace of washing buffer and to be under optimal conditions for the elution step.

The following table compares the results obtained with the device according to the invention when applying the protocol that has just been described (2 first washing operations followed by a third washing operation with release of the particles) in comparison with the results obtained with a device of the prior art, namely the MiniMag® sold by the company bioMérieux and considered to be a reference device in viral RNA extraction. The protocol for the MiniMag® comprises four washing steps with the washing buffers (two with the "NucliSENS easyMAG Extraction Buffer No. 1" and two with the "NucliSENS easyMAG Extraction Buffer No. 2"). In order to determine the efficiency of the extraction, a real-time PCR amplification (or "q-PCR") of the lysate extracted is carried out and the Ct ("cycle threshold", which quantifies a threshold of detection of nucleic acid in a sample) of each sample is measured. The samples tested in duplicate are samples of 25 grams of raspberry or of green onion to which is added a solution of Mengo virus which is pure (corresponding to 500 copies of the genome per 25 grams) or diluted to $1/10^{th}$.

| Sample | | Invention (Ct value) | | MiniMag® (Ct value) | |
|---|---|---|---|---|---|
| | | Raspberry | Green Onion | Raspberry | Green Onion |
| Mengo | pure | 25.72  26.29 | 25.87  25.55 | 24.86 | 25.06 |
| | 1/10 | 27.87  28.61 | 28.06  27.95 | 28.01 | 27.81 |
| Mengo | pure | 26.05  26.11 | 25.82  25.87 | 24.93 | 24.99 |
| | 1/10 | 28.23  28.44 | 27.59  28.13 | 28.06 | 27.76 |

As can be seen, the extraction of the viral RNA according to the invention gives results similar to those obtained using the MiniMag®. In addition, tests were carried out with various batches of magnetic silica particles of diverse quality. It was noted that the extraction according to the invention is surprisingly very robust with respect to the quality of said particles. In particular, tests were carried out on the same samples with a batch of particles of lower performance grade, the extraction not comprising the release/washing/recapture step as previously described. In this case, the degree of extraction was lower. When using the preferred method previously described with the defective particles, results similar to those of the preceding table were obtained.

An application of the invention to the capture of nucleic acids, e.g. RNA and/or DNA, originating from a lysis carried out before the capture/washing/migration and transfer phases, has been described. The invention also applies to the capture of microorganisms (e.g. bacteria, fungi, yeasts) by means of magnetic particles of which the surface is functionalized so as to capture the microorganisms (e.g. covered with phage proteins or with polycations suitable for such a capture in a manner known per se). The magnetic particles with their captured microorganisms are transferred into tubes in order to subsequently undergo lysis, for example mechanical lysis. The lysate obtained can directly be the subject of a treatment, for example a polymerase chain reaction amplification (e.g. a quantitative PCR of q-PCR type), or can be purified according to the nucleic acid extraction method previously described.

The invention is particularly suitable for the preparation of a microbial sample for the purpose of a PCR. Indeed, the sample on which the capture of particles in the pipette cones is carried out may have a very large volume (e.g. several milliliters), whereas the final volume of the tubes into which the particles are transferred can be very small (e.g. less than or equal to 200 microliters, or even less than or equal to 100 microliters). Because of the large volume of the sample, a large number of microorganisms are captured. The passage to a very small final volume has the effect of concentrating the microorganisms. Thus, the inventors have noted that a single phase of capture from a sample of a few milliliters, followed by a single washing step, is sufficient to obtain results by q-PCR from a lysis carried out in a volume of 5 microliters.

In particular, an enrichment of food matrix (chicken aiguillette) with nutritive broth was carried out for 5 h at 41.5° C. A post-contamination with a *Salmonella derby* strain is carried out at a level of $10^2$ to $10^4$ CFU/ml, which corresponds to concentrations that can be reached after enrichment in the presence of pathogen in the food matrix (i.e. concentrations for which a food batch is determined to be unfit for consumption). Two procedures were carried out, in duplicate, on each contaminated sample, one according to a standardized capture protocol with the Gene-up® system from bioMérieux, France, and one according to the invention.

The Gene-up protocol consists of a step of "bead-beating" of the sample (i.e. mechanical disruption of the wall of the bacteria), by taking 20 µl of said sample and placing it in a bead-beating tube containing 180 µl of washing buffer, followed by shaking for 5 minutes on a microplate shaker for bead-beating. 5 microliters of the final solution are taken and are subjected to a q-PCR.

The method according to the invention consists, for its part, of:
1. a specific capture step by bringing 2 ml of sample into contact with a biotinylated phage protein solution (final concentration 2 µg/ml) by:
   a. agitating by suction/discharge in the pipette cones for 10 min;
   b. adding "Hyglos Streptavidin" magnetic particles (50 µl) and agitating by suction/discharge for 15 minutes (the bacteria-biotinylated phage protein complexes bind to the magnetic particles);
   c. putting in place the magnet for the phase of collecting the magnetic particles in the cones;
   d. launching the magnetic particle capture cycle;
2. a step of washing in the wells containing the TST (Tris Saline Tween) washing solution with 5 suction/discharge cycles;
3. a step of collecting the magnetic particles in the 5-microliter tubes which are subjected to a bead-beating treatment, the final solution of 5 microliters then being subjected to a q-PCR.

The results obtained according to the Gene-up® protocol and according to the invention are summarized in the table below:

| Concentration | Invention (Ct value) | Gene-up ® (Ct value) |
|---|---|---|
| $10^2$ CFU/ml | 35.2 | No Ct |
| | 35 | No Ct |
| $10^3$ CFU/ml | 33.8 | No Ct |
| | 33.8 | No Ct |
| $10^4$ CFU/ml | 29.5 | 34.9 |
| | 29.7 | No Ct |

The estimated gain in sensitivity is 2 log compared with the Gene-up standard protocol.

The present invention answers a problem of polyvalence for the use of various magnetic capture techniques (nucleic acid purification, magnetic immunoconcentration, etc.). The system according to the invention, which is evolutive and modulatable, allows:
steps of capture/washing/elution of magnetic particles to be carried out using an autonomous system consisting of the combination of a programmable electronic pipette and of a support enabling the various above-mentioned steps to be carried out;

a number of samples of 1 to 8 to be treated as a function of the configuration of the electronic pipette used;

the samples to be treated in parallel in the context defined above with a semi-automatic system;

2 systems to be combined if required to increase the number of samples to be treated;

it to be possible for the elution steps to be carried out in various types of tubes: 0.2 ml PCR tubes for recovering the magnetic silica particles when nucleic acid capture is involved (e.g. NucliSENS© chemistry) or else bead-beating tubes in the case of the recovering of magnetic particles having been used for the recovery of pathogens (magnetic immunoconcentration). To this end, the system makes it possible to carry out steps of capture/concentration of pathogens on the magnetic particles and the in situ lysis thereof by means of ceramic/glass beads (e.g. method of CapLyse© type).

The invention claimed is:

1. A pipette holder comprising:
a base;
a recess made in the base, the recess removably housing a well support;
a pipette support comprising a first housing into which a pipette is removably inserted, the pipette support equipped with one or more tubular pipette cones wherein each pipette cone comprises a tip intended for pipetting a liquid from a well of the well support, the liquid containing magnetic particles, the first housing opening out onto the recess of the base, the pipette support configured to translationally move relative to the base in a direction parallel to an axis of the pipette cones and to move from a first position in which the tip of each pipette cone is inserted in the well of the well support to a second position in which the tip is outside the well;
a second housing removably housing a magnetized part, the second housing facing each of the pipette cones in a position above the tip thereof when the pipette support is in the first position, and the second housing facing the tip of the pipette cone when the pipette support is in the second position
wherein the magnetized part is configured to produce a first magnetic field to the pipette cone containing the liquid containing magnetic particles thereby attracting and holding the magnetic particles in a predetermined zone of the pipette cone above the tip of the cone, the magnetized part configured to produce a second magnetic field from the bottom of a recovery well when the magnetized part is positioned partially or entirely under the tip of the pipette cone so as to cause the magnetic particles contained in the tip of the pipette cone to migrate into the recovery well.

2. The pipette holder as claimed in claim 1, wherein the first housing comprises an opening for a frontal insertion of the pipette into and a frontal removal of the pipette from the first housing.

3. The pipette holder as claimed in claim 1, wherein the second housing is made in the base.

4. The pipette holder as claimed in claim 1, comprising a third housing in the pipette support into which the magnetized part is removably inserted in order to face each pipette cone at a position above the tip of the cone when the pipette support is in the second position.

5. The pipette holder as claimed in claim 4, wherein the second and third housings communicate, and wherein the pipette support comprises means capable of removably maintaining the magnetized part in the third housing.

6. The pipette holder as claimed in claim 1, wherein:
the base comprises at least one toothed wheel configured to rotate; and
the pipette support comprises a rack which engages with the toothed wheel in order to translationally move the pipette support relative to the base during a rotation of the toothed wheel.

7. The pipette holder as claimed in claim 6, comprising a device for locking and unlocking the pipette support at least in the first position.

8. The pipette holder as claimed in claim 6, comprising at least one handle rigidly connected to the toothed wheel for turning the wheel and capable of removably attaching to a handle rigidly connected to the toothed wheel of another pipette holder.

9. A system for extracting components contained in a biological sample in liquid form, the components being capable of binding to magnetic particles, the system comprising:
a pipette equipped with one or more tubular pipette cones that each comprise a tip intended for pipetting liquid and with a circuit for suction and discharge in each pipette cone;
at least one well support; and
the pipette holder as claimed in claim 1.

10. The system as claimed in claim 9, wherein the first housing comprises an opening for a frontal insertion of the pipette into and a frontal removal of the pipette from the first housing.

11. The system as claimed in claim 9, wherein the second housing is made in the base.

12. The system as claimed in claim 9, wherein the pipette holder comprises a third housing in the pipette support into which the magnetized part is removably inserted in order to face each pipette cone at a position above the tip of the cone when the pipette support is in the second position.

13. The system as claimed in claim 12, wherein the second and third housings communicate, and wherein the pipette support comprises means capable of removably maintaining the magnetized part in the third housing.

14. The system as claimed in claim 9, wherein: the base comprises at least one toothed wheel configured to rotate; and
the pipette support comprises a rack which engages with the toothed wheel in order to translationally move the pipette support relative to the base during a rotation of the toothed wheel.

15. The system as claimed in claim 14, wherein the pipette holder comprises a device for locking and unlocking the pipette support at least in the first position.

16. The system as claimed in claim 14, wherein the pipette holder comprises at least one handle rigidly connected to the toothed wheel for turning the wheel and capable of removably attaching to a handle rigidly connected to the toothed wheel of another pipette holder.

17. The system as claimed in claim 9, wherein the well support comprises a part in which recesses for receiving the wells are made, and at least one magnet facing each of the recesses made in the part.

* * * * *